(12) United States Patent
Jared

(10) Patent No.: US 7,611,456 B2
(45) Date of Patent: Nov. 3, 2009

(54) MALE SEXUAL AID AND METHOD

(76) Inventor: Roy A. Jared, 2527 Albion St., Denver, CO (US) 80207

( * ) Notice: Subject to any disclaimer, the term of this patent is extended or adjusted under 35 U.S.C. 154(b) by 293 days.

(21) Appl. No.: 11/535,846

(22) Filed: Sep. 27, 2006

(65) Prior Publication Data

US 2008/0076964 A1    Mar. 27, 2008

(51) Int. Cl.
*A61F 5/00* (2006.01)
(52) U.S. Cl. ............................................. 600/39
(58) Field of Classification Search ........... 128/897, 128/898; 600/38–41
See application file for complete search history.

(56) References Cited

U.S. PATENT DOCUMENTS

| | | | | |
|---|---|---|---|---|
| 1,585,861 | A | * | 5/1926 | Huff .............................. 600/39 |
| 3,446,206 | A | * | 5/1969 | De Lano ....................... 600/39 |
| 3,920,007 | A | | 11/1975 | Line |
| 4,262,662 | A | | 4/1981 | Allinson |
| 4,449,521 | A | | 5/1984 | Panzer |
| 4,672,954 | A | | 6/1987 | Panzer |
| 5,360,390 | A | | 11/1994 | Maanum |
| 5,800,340 | A | | 9/1998 | Gekhter et al. |
| 5,928,134 | A | | 7/1999 | Vergara |
| 6,186,943 | B1 | | 2/2001 | Pan |
| 6,436,031 | B1 | * | 8/2002 | Salib ............................ 600/39 |
| 6,793,620 | B1 | | 9/2004 | Droznin et al. |

OTHER PUBLICATIONS

"Premature Ejaculation: The Most Common Male Sexual Dysfunction," Clinical Courier, 24(22):1-8, ISSN 0264-6684 (Jun. 2006).

* cited by examiner

*Primary Examiner*—Samuel G Gilbert

(57) ABSTRACT

A male sexual aid and a method for supporting a male sexual organ. An external splint is manufactured by forming a base adjacent to one end of a support and an introducer adjacent an opposing end of the support. The support may include a single support member or a plurality of support members. The base may be a ring structure through which a penis is inserted and the introducer may be a ring structure on which the glans penis is preferably positioned. The glans penis is elastically coupled to the external splint. By way of example, an elastic band having an orifice is coupled to the splint and the penis is inserted through the orifice so that a shoulder of the glans penis is adjacent the elastic band.

29 Claims, 3 Drawing Sheets

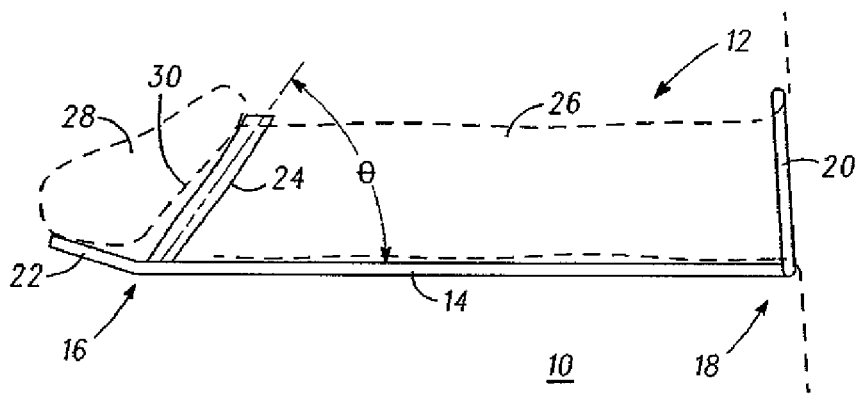
FIG. 1
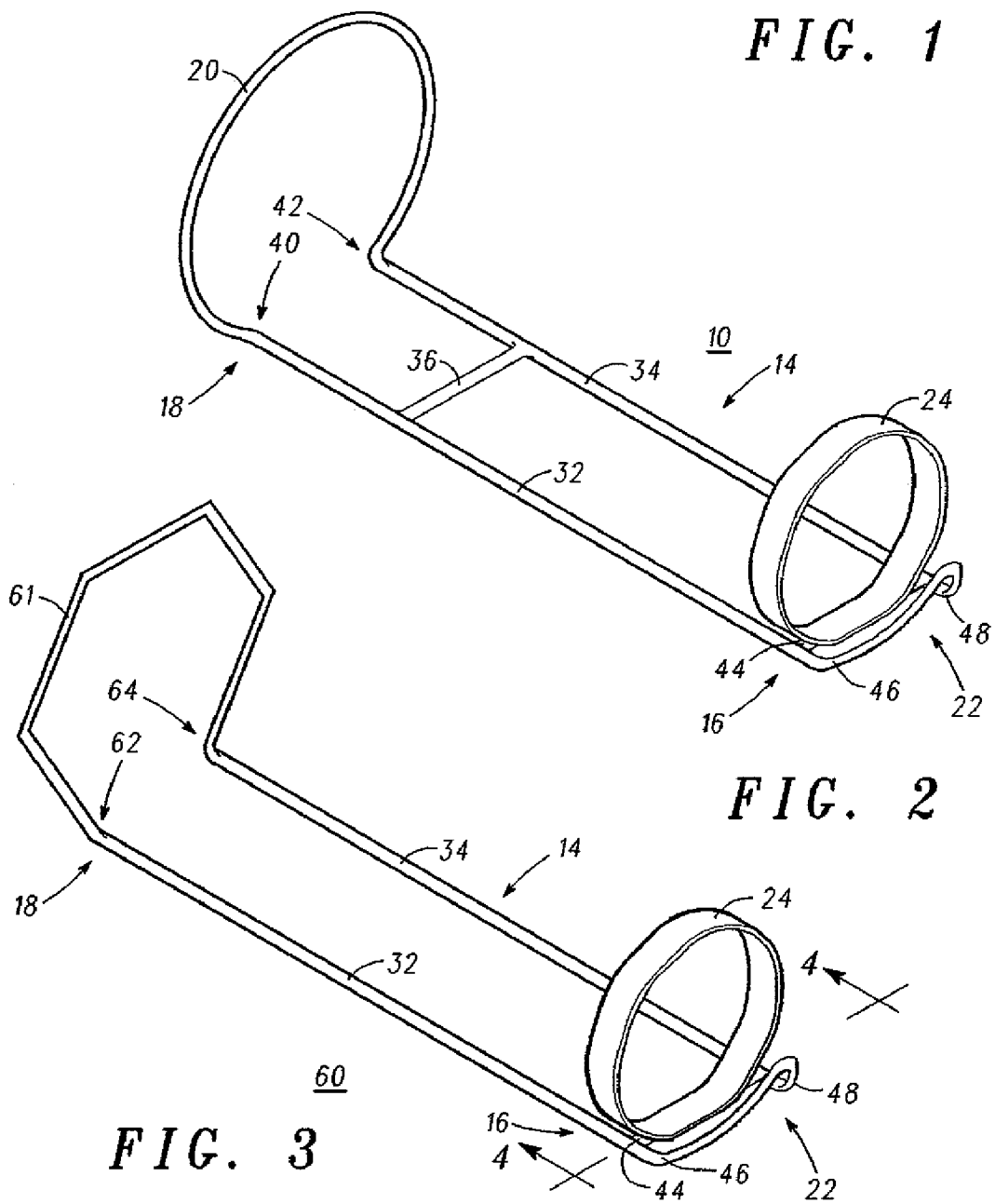
FIG. 2
FIG. 3

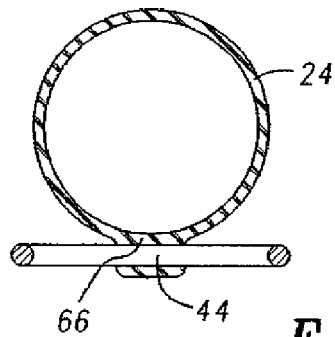
FIG. 4
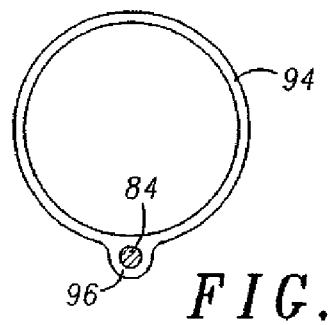
FIG. 6
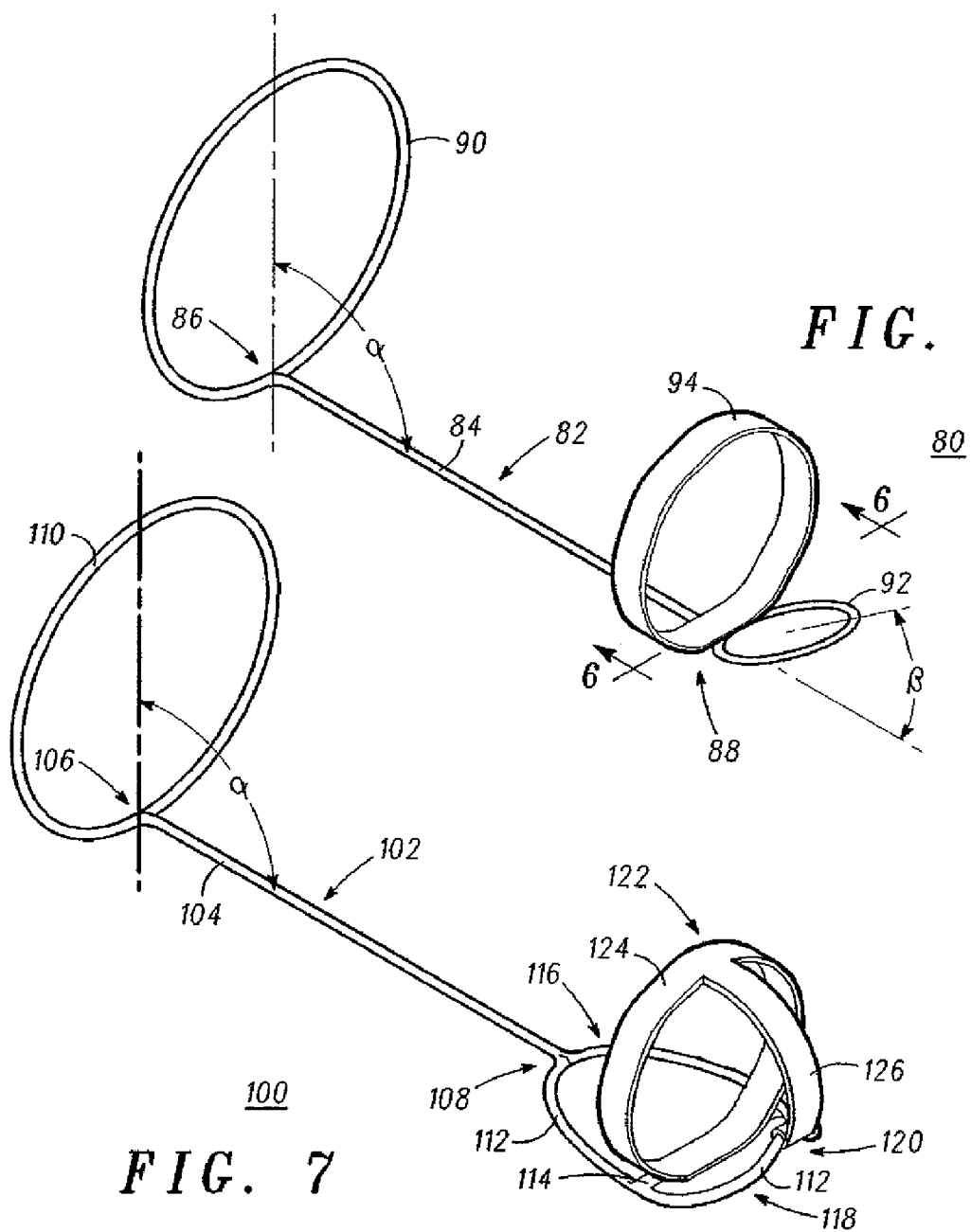
FIG. 5
FIG. 7

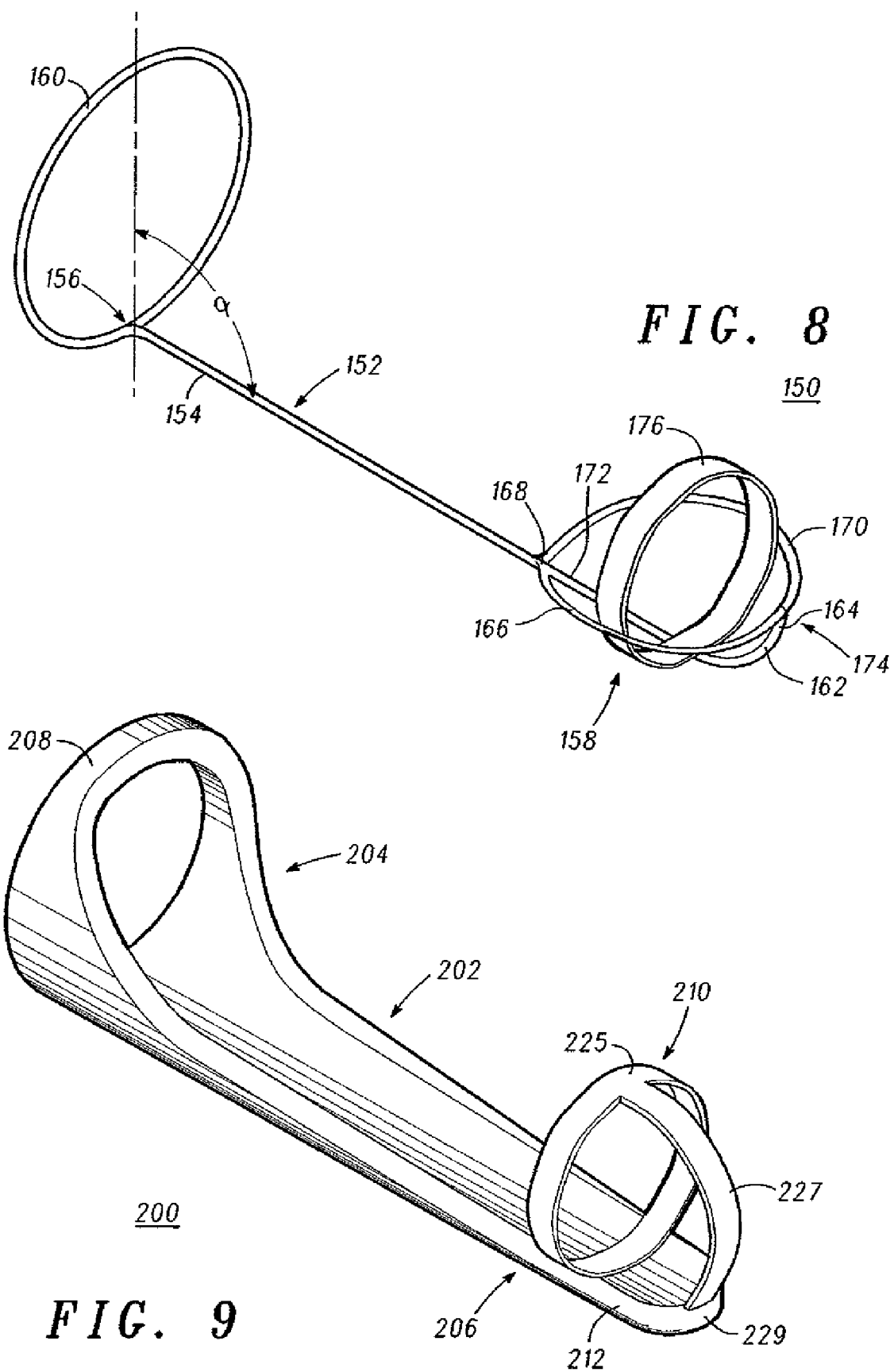

MALE SEXUAL AID AND METHOD

FIELD OF THE INVENTION

The present invention relates, in general, to a male sexual aid and, more particularly, to a male splint.

BACKGROUND OF THE INVENTION

During normal sexual relations, the act of sexual intercourse involves the insertion of an erect male penis into the vagina of a female. In men with a sexual dysfunction, there is difficulty with at least one stage of the sexual act. Two of the most common sexual problems men experience are erectile dysfunction and premature ejaculation. Erectile dysfunction is characterized by the inability of the male to achieve or maintain an erection which may preclude the performance of the sexual act that is pleasing to the partners. This problem is independent of ejaculation. Typical treatments for erectile dysfunction include pharmacologic agents such as sildenafil, vardenafil, tadilafil, or mechanical means such as surgical implants, vacuum tumescence, constrictor bands, and splints. Although these treatments have resulted in varying degrees of success, they also offer drawbacks for one or both sexual partners. For example, the pharmacologic agents may have adverse side effects or drug-drug interactions that are harmful to the user. The mechanical means are oftentimes complicated for the user to attach and they may be uncomfortable for the male partner, female partner, or both partners due to shapes that can poke, pinch, or entangle hair. For example, U.S. Pat. No. 3,446,206 to De Lano includes a penetrator rod that must be inserted into the urethra of the penis. Another drawback with the mechanical means has been that they limit the amount of direct contact between the penis and the vagina, thereby degrading the sensual and intimate aspects of the sexual act. In addition, they may include features that are hard to clean and which can increase the chance of infectious disease transmission. Another drawback with mechanical means is their difficulty in withstanding the insertion forces associated with penetrating the vagina. For satisfactory insertion of the glans penis into the vagina, it has the difficult task of overcoming the resistance presented by the vaginal introitus.

Although these pharmacological and mechanical means have had limited success at addressing erectile dysfunction, they have been less successful at addressing premature ejaculation. The definition of premature ejaculation of the American Urologic Association is "[e]jaculation that occurs sooner than desired, either before or shortly after penetration, causing distress to either one or both partners." Typically, approaches for dealing with premature ejaculation have been limited to using topical or ingested medications, using behavioral therapies, decreasing the sensation on the penis, or combinations thereof.

Accordingly, it would be advantageous to have an apparatus and method for ameliorating erectile dysfunction, premature ejaculation, or both. It would be of further advantage for the apparatus and method to be easy and inexpensive to implement.

SUMMARY OF THE INVENTION

The present invention satisfies the foregoing advantages by providing a male sexual aid and a method for manufacturing the male sexual aid. In accordance with one embodiment, a male reproductive organ is mounted over a support structure. A portion of the male reproductive organ is elastically coupled to the support structure. Thus, a method for supporting a male reproductive organ is provided.

In accordance with another embodiment of the present invention, a penis is positioned over a splint and a portion of the penis is expandably mated to the splint, wherein the penis can change erectile states. Thus, a method for compensating for male erectile dysfunction is provided.

In accordance with another embodiment of the present invention, a method for manufacturing a male splint is provided. A support structure having first and second ends is provided and a base is formed at or adjacent the first end and an introducer is formed at or adjacent the second end. An elastic material is coupled to or adjacent to the second end, wherein the elastic material covers less than half of the penis.

In accordance with another embodiment, an external penile splint is provided that comprises a support having first and second ends. A base is located at or adjacent to the first end and an introducer is located at or adjacent to the second end. An elastic structure is coupled adjacent to the introducer.

BRIEF DESCRIPTION OF THE DRAWINGS

The present invention will be better understood from a reading of the following detailed description, taken in conjunction with the accompanying drawing figures, in which like reference characters designate like elements and in which:

FIG. 1 is a side view of an external male splint including a penis in accordance with an embodiment of the present invention;

FIG. 2 is an isometric view of the external male splint of FIG. 1;

FIG. 3 is an isometric view of an external male splint in accordance with another embodiment of the present invention;

FIG. 4 is a cross-sectional view of a portion of the male splints of FIGS. 2 and 3 accordance with an embodiment of the present invention;

FIG. 5 is an isometric view of an external male splint in accordance with another embodiment of the present invention;

FIG. 6 is a cross-sectional view of a portion of the male splint of FIG. 5 in accordance with an embodiment of the present invention;

FIG. 7 is an isometric view of an external male splint in accordance with another embodiment of the present invention;

FIG. 8 is an isometric view of an external male splint in accordance with another embodiment of the present invention; and FIG. 9 is an isometric view of an external male splint in accordance with another embodiment of the present invention.

DETAILED DESCRIPTION

Generally, the present invention provides a male sexual aid and a method for mitigating erectile dysfunction and premature ejaculation. In accordance with one embodiment, the male sexual aid is a splint that includes a support structure having a base at or adjacent to one end and an introducer at or adjacent to an opposing end, wherein the introducer is ring shaped. The introducer is for opening and overcoming the resistance of the vaginal introitus. An elastic structure or material such as, for example, an elastic band having an orifice is coupled to a portion of the splint adjacent the introducer. The elastic structure serves as an expandable mating portion or an expandable coupler. The penis is inserted through the base and through the orifice of the elastic band. The elastic band may serve as a tether for maintaining a positional relationship between the penis whereas the introducer helps overcome resistance associated with penetrating the introitus of the vagina. Coupling the penis to the splint using an elastic band is also referred to as expandably mating a portion of the penis to the splint. An advantage of the elastic band is that it can accommodate a penis that is not erect or that is partially erect, i.e., it can accommodate a penis experiencing erectile dysfunction or that has changed erectile states. In other words, the elastic band can accommodate an erect penis, a partially erect penis, or a non-erect penis. In addition, the base cooperates with the elastic band so that a male who experiences premature ejaculation or loss of his erection can maintain his penis in his partner's vagina thereby allowing them to continue with sexual intercourse, which would typically end with the loss of an erection. The splint can be a unitary structure in which the support structure, the base, and the introducer are manufactured as a single structure. Alternatively, the base, the introducer, or both may be coupled to the support structure.

In accordance with another embodiment, the introducer has the shape of a basket and the elastic band comprises a ring or a ring-like structure having an extension. A portion of the elastic band is attached to the support structure and the extension is attached to another portion of the support structure.

In accordance with yet another embodiment, the splint is made from plastic and has a ring or ring-like base structure at one end that tapers towards an opposing end.

FIG. 1 is a side view of an external male splint 10 in accordance with an embodiment of the present invention. What is shown in FIG. 1 is a penis 12 inserted into an external male splint 10, which comprises a support structure 14, a base 20, an introducer 22, and an elastic band 24. Support structure 14 has an end 16 and an end 18. Base 20 is formed at or adjacent to end 18 and introducer 22 is formed at or adjacent to end 16. A male reproductive organ such as a penis 12 comprises a shaft 26 having an end 28 which is also referred to as the glans penis. Shaft 26 has a ventral side and a dorsal side and the glans penis 28 has a shoulder 30. The glans penis 28 is inserted through base 20 so that penis 12 is supported by support structure 14. Preferably, the ventral side of shaft 26 is positioned on support structure 14 and the glans penis 28 is positioned on introducer 22. Although the glans penis 28 is shown as being positioned on introducer 22, this is not a limitation of the present invention. The glans penis 28 can be positioned so that it is spaced apart from introducer 22. However, it is desirable that the distance or spacing between the glans penis 28 and introducer 22 be such that introducer 22 provides support for the glans penis 28. Preferably, the distance between the glans penis 28 and introducer 22 is less than about 0.25 inches. Thus, a thin structure such as, for example, a condom would not interfere with introducer 22. It should be understood that the location of splint 10 is not a limitation of the present invention. For example, it can be positioned so that support structure 14 contacts the ventral side of shaft 26 or that support structure 14 contacts one or both of the lateral sides of shaft 26. The lateral sides of shaft 26 are the sides extending from the dorsal and ventral sides of shaft 26.

In addition to being inserted through base 20, penis 12 is also inserted through elastic band 24. Preferably, elastic band 24 is aligned with shoulder 30 of the glans penis 28 and makes an angle θ with respect to shaft 26. By way of example, angle θ ranges from approximately 40 degrees to approximately 50 degrees. It should be noted that the angle will vary depending on the resistance encountered by the glans penis 28. When there is less resistance, the angle is greater, i.e., the angle decreases as the resistance experienced by the glans penis 28 increases.

FIG. 2 is an isometric view of external male splint 10 in accordance with an embodiment of the present invention. Support structure 14 comprises a pair of support members 32 and 34 that may be substantially parallel to each other. Support member 32 is connected to support member 34 by a cross-member 36. Cross-member 36 is shown as being spaced apart from end 18. By way of example, cross-member 36 may be positioned at a distance of about one-third the length of support members 32 and 34. Rather than being spaced apart from end 18, cross-member 36 could be positioned at end 18. Thus, the location of cross-member 36 is not a limitation. Base 20 comprises an open circular structure having ends 40 and 42, wherein the portion within the open circular structure serves as an opening. End 40 of the open circle is connected to support member 32 and end 42 of the open circle is connected to support member 34. Suitable materials for support structure 14 include carbon fibers, fiberglass, stainless steel, or the like.

A cross-member 44 is connected between support members 32 and 34 near end 16 of support structure 14. Introducer 22 extends from support members 32 and 34. By way of example, introducer 22 is an inverted V-shaped structure having ends 46 and 48 connected to support members 32 and 34, respectively. The apex of V-shaped introducer 22 extends upward at an angle in a fashion similar to the tip of a snow ski. In other words the apex extends away from support members 32 and 34. Elastic band 24 may be connected to cross-member 44.

In use, a penis such as, for example, penis 12 shown in FIG. 1 is mounted to support structure 14 by inserting it through the opening in base 20 and through elastic band 24 so that shaft 26 of penis 12 is positioned on support members 32 and 34 and elastic band 24 is adjacent glans penis 28. A portion of penis 12 is elastically coupled to support structure 14. More particularly, a portion of penis 12 adjacent the glans penis 28 is elastically coupled to support structure 14. Thus, splint 10 provides support for a penis that may be experiencing erectile dysfunction. In addition, base 20 cooperates with elastic band 24 so that a male who experiences premature ejaculation or loss of his erection can maintain his penis in his partner's vagina thereby allowing them to continue with sexual intercourse, which would typically end with the loss of an erection.

FIG. 3 is an isometric view of an external male splint 60 in accordance with another embodiment of the present invention. Like splint 10, splint 60 includes a support structure 14, an introducer 22, and an elastic band 24. Splint 60 further includes a base 61 that is a polygonal-shaped opened ring structure having ends 62 and 64. End 62 of the polygonal-shaped opened ring structure is connected to support member 32 and end 64 of the polygonal-shaped open ringed structure is connected to support member 34.

Splint 60 also includes cross-member 44 connected between support members 32 and 34 near end 16 of support structure 14. Introducer 22 extends from support members 32 and 34. By way of example, introducer 22 is an inverted V-shaped structure having ends 46 and 48 connected to support members 32 and 34, respectively. The apex of V-shaped introducer 22 extends upward at an angle and in a fashion similar to the tip of a snow ski. Elastic band 24 is connected to cross-member 44.

Splint 60 is used in a fashion similar to that of splint 10.

FIG. 4 is a cross-sectional view of an elastic band and a cross-member of splints 10 and 60 shown in FIGS. 2 and 3.

More particularly, FIG. 4 illustrates an embodiment of a technique for attaching elastic band 24 to cross-member 44. In accordance with the embodiment shown in FIG. 4, elastic band 24 has an extension 66 through which cross-member 44 extends. Thus, elastic band 24 is fastened or attached to support structure 14 through cross-member 44. Elastic band 24 may be tied to cross-member 44, glued to cross-member 44, clipped to cross-member 44, molded around cross-member 44, or the like. It should be understood that the method for attaching elastic band 24 to cross-member 44 is not a limitation of the present invention. Alternatively, elastic band 24 may be fastened or attached to introducer 22.

FIG. 5 is an isometric view of an external male splint 80 in accordance with another embodiment of the present invention. Splint 80 includes a support structure 82 comprising a support member 84 having ends 86 and 88. A base 90 is connected at or adjacent to end 86 of support member 84 and an introducer 92 is connected at or adjacent to end 88 of support member 84. In accordance with one embodiment, base 90 comprises a circular structure having an opening, wherein the base makes an angle α with support member 84 and introducer 92 comprises a circular structure that makes an angle β with support member 84. By way of example, angle α is substantially equal to approximately 90 degrees and angle β is less than approximately 90 degrees. A suitable range of angles for angle β is from approximately 30 degrees to approximately 50 degrees. It should be noted that the shapes of base 90 and introducer 92 and the values of angles α and β are not limitations of the present invention.

An elastic band 94 is connected to end 88 of support member 84. It should be noted that elastic band 94 can be connected to introducer 92 or to a point along support member 84. Preferably, elastic band 94 is connected to a connection point located between end 88 of support member 84 and introducer 92. It should be further noted that elastic band 94 can be attached so that it is movable along support member 84 to allow movable coupling of elastic band 94 to support member 84 thereby allowing adjustment by the user for optimal function.

Splint 80 is used in a similar way as splints 10 and 60. A penis 12 is inserted through the opening in base 90 and elastic band 94 so that shaft 26 of penis 12 is positioned on support member 84 and elastic band 94 is adjacent glans penis 28. Thus, splint 80 provides support for a penis that may be experiencing erectile dysfunction. In addition, base 90 cooperates with elastic band 94 so that a male who experiences premature ejaculation or loss of his erection can maintain his penis in his partner's vagina thereby allowing them to continue with sexual intercourse, which would typically end with the loss of an erection.

FIG. 6 is a cross-sectional view of a support member extending through a portion of an elastic band. By way of example, FIG. 6 is a cross-sectional view taken along section line 6-6 of FIG. 5 and shows portions of support member 84 and elastic band 94. In addition, FIG. 6 illustrates an embodiment for connecting elastic band 94 to support member 84. In this embodiment, elastic band 94 has a mating section 96 through which support member 84 extends. Elastic band 94 may be attached to support member 84 by wrapping a portion of mating section 96 around support member 84 and attaching it to another portion of mating section 96. The two portions of mating section 96 may be attached using a string, a nylon line, staples, through the use of an adhesive, by melting the two portions together, or the like. It should be understood that the method for attaching elastic band 94 to support member 84 is not a limitation of the present invention.

FIG. 7 is an isometric view of an external male splint 100 in accordance with another embodiment of the present invention. Splint 100 includes a support structure 102 comprising a support member 104 having ends 106 and 108. A base 110 is connected at or adjacent to end 106 of support member 104 and an introducer 112 is connected at or adjacent to end 108 of support member 104. In accordance with one embodiment, base 110 comprises a circular structure having an opening, wherein the circular structure makes an angle α with support member 104. By way of example, angle α is substantially equal to approximately 90 degrees. Introducer 112 is a ring structure having a cross-member 114 extending from one side of the ring structure to an opposite side of the ring structure thereby dividing the ring structure into two portions 116 and 118. Portion 116 extends from end 108 to cross-member 114 and portion 118 extends from cross-member 114 to a fastening portion 120. Preferably, portion 116 is substantially planar and portion 118 extends upward at an angle in a fashion similar to the tip of a snow ski.

An elastic band 122 is connected to support structure 102. Elastic band 122 has a ring-shaped body 124 and an elastic extension 126 extending from one side of ring-shaped body 124. Ring-shaped portion 124 may be attached to cross-member 114 just as elastic band 24 is attached to cross-member 44 as described with reference to FIG. 4. In addition, an end of elastic extension 126 is attached to fastening portion 120 using, for example, an adhesive material. The methods for attaching elastic band 122 to cross-member 114 and for attaching elastic extension 126 to fastening portion 120 are not limitations of the present invention.

Splint 100 is used in a similar way as splints 10, 60, and 80. A penis 12 is inserted through the opening in base 110 and through elastic band 122 so that shaft 26 of penis 12 is positioned on support member 104 and ring-shaped body 124 of elastic band 122 is adjacent shoulder 30 of the glans penis 28. Thus, splint 100 provides support for a penis that may be experiencing erectile dysfunction. In addition, base 110 cooperates with elastic band 122 so that a male who experiences premature ejaculation or loss of his erection can maintain his penis in his partner's vagina thereby allowing them to continue with sexual intercourse, which would typically end with the loss of an erection.

FIG. 8 is an isometric view of external male splint 150 in accordance with another embodiment of the present invention. Splint 150 includes a support structure 152 comprising a support member 154 having ends 156 and 158. A base 160 having an opening is connected at or adjacent to end 156 of support member 154. End 158 has a bend 162 and a tip 164, wherein the bend extends tip 164 in a similar direction that base 160 extends. A curved support element 166 extends from an extension point 168 of support member 154 to tip 164 and another curved support element 170 extends from extension point 168 to tip 164. Curved support element 166, curved support element 170, and the portion 172 of support member 154 that extends from extension point 168 to tip 164 cooperate to form an introducer 174. End 158, tip 164, and curved support elements 166 and 170 cooperate to form a basket structure. Although introducer 174 and support element 154 are shown as a unitary structure, this is not a limitation of the present invention. For example, introducer 174 and support element 154 can be separate elements that are connected together.

An elastic band 176 is connected to portion 172 of support member 154. Elastic band 176 is a ring-shaped structure that may be attached to portion 172 just as elastic band 94 is attached to support member 84 as described with reference to FIG. 5. Alternatively, elastic band 176 may be attached to portion 172 of support member 154 and to curved support element 166, or to portion 172 of support member 154 and to curved support element 170, or to portion 172 of support member 154 and to curved support elements 166 and 170, or to curved support element 166, or to curved support element 170, etc. The method for attaching elastic band 176 to introducer 174 is not a limitation of the present invention. Elastic band 176 can be attached so that it is movable along portion 172 of support member 154 to allow adjustment by the user for optimal function.

Splint 150 is used in a similar way as splints 10, 60, 80, and 150. A penis 12 is inserted through the opening in base 160 and elastic band 176 so that shaft 26 of penis 12 is positioned on support member 154 and elastic band 176 is adjacent the glans penis 28. Thus, splint 150 provides support for a penis that may be experiencing erectile dysfunction. In addition, base 160 cooperates with elastic band 176 so that a male who experiences premature ejaculation or loss of his erection can maintain his penis in his partner's vagina thereby allowing them to continue with sexual intercourse, which would typically end with the loss of an erection.

FIG. 9 is an isometric view of an external male splint 200 in accordance with another embodiment of the present invention. Splint 200 includes a support structure 202 having an end 204 and an end 206. A base or ring structure 208 having an opening is formed from an end 204. In accordance with one embodiment, support structure 202 is tapered in a direction from ring structure 208 towards end 206. By way of example, support structure 202 is a molded structure made from plastic. Other suitable materials for support structure 202 include rubber or the like. Portion 212 serves as an introducer.

An elastic band 210 is connected to support structure 202. Elastic band 210 has a ring-shaped body 225 and an elastic extension 227 extending from one side of ring-shaped body 225. Ring-shaped body 225 may be attached near an end of support structure 202. In addition, the end of elastic extension 227 is attached to fastening portion 229 using, for example, an adhesive material. The methods for attaching elastic band 210 to support structure 202 and for attaching elastic extension 227 to fastening portion 229 are not limitations of the present invention.

Splint 200 is used in a similar way as splints 10, 60, 80, 150, and 200. A penis 12 is inserted through the opening of base 208 and ring-shaped body 225 of elastic band 210 so that shaft 26 of penis 12 is positioned on support structure 202 and elastic band 210 is adjacent the glans penis 28. Thus, splint 200 provides support for a penis that may be experiencing erectile dysfunction. In addition, base 208 cooperates with elastic band 210 so that a male who experiences premature ejaculation or loss of his erection can maintain his penis in his partner's vagina thereby allowing them to continue with sexual intercourse, which would typically end with the loss of an erection.

By now it should be appreciated that a male sexual aid has been provided that mitigates erectile dysfunction and premature ejaculation. In accordance with an embodiment the male sexual aid is an external or non-invasive splint. An advantage of the splint in accordance with the various embodiments is that it is non-invasive, i.e., it is not inserted into the penis, and does not involve the use of pharmacological agents that may be deleterious to the user. The splint is as easy to use as a condom, which can be readily put on in complete darkness. In addition, the male splint leaves at least seventy-five percent of the male reproductive organ exposed so that there is a minimal reduction in sensory perception between the female and male partners which increases the intimacy of the sexual act and the physical pleasure. Another advantage is that by using an elastic band to extend the shaft of the penis and hold the glans penis in position on the splint, any degree of erection can be accommodated. Because any degree of erection can be accommodated these splints can aid men with premature ejaculation as well as erectile dysfunction. The elastic bands can be attached so that they are movable on the support to allow adjustment by the user for optimal function as described with reference to splints 80 and 150 of FIGS. 5 and 8, respectively. Another advantage is that the splints described for the various embodiments are comfortable to wear including wearing them under clothing, if desired. Their shapes are smooth and rounded to enhance comfort for the female partner. The shape and position of the introducer aids in opening and overcoming the resistance of the vaginal introitus concurrently with the entry of the glans penis. What's more, condoms can be readily used in conjunction with the splints for either infection prevention or pregnancy prevention or both. The condom can easily be used either under the splint or covering both the penis and the splint.

Although certain preferred embodiments and methods have been disclosed herein, it will be apparent from the foregoing disclosure to those skilled in the art that variations and modifications of such embodiments and methods may be made without departing from the spirit and scope of the invention. It is intended that the invention shall be limited only to the extent required by the appended claims and the rules and principles of applicable law.

What is claimed is:

1. A method for supporting a male reproductive organ, comprising:
   providing a support structure having a base, an introducer, and first and second ends, wherein the base is adjacent the first end and the introducer is adjacent the second end;
   coupling an elastic band to the support structure, wherein the elastic band is capable of covering less than half of the male reproductive organ, has a first opening through which the male reproductive organ can be inserted and a second opening through which the support structure is inserted, the second opening smaller than the first opening, and wherein coupling the elastic band to the support structure includes slidably coupling the elastic band to the support structure so that the elastic band can be moved between the first and second ends to allow adjustment by the user;
   mounting the male reproductive organ over the support structure; and
   elastically coupling a portion of the male reproductive organ to the support structure by inserting the male reproductive organ through the first opening of the elastic band.

2. The method of claim 1, wherein elastically coupling the portion of the male reproductive Organ to the support structure includes elastically coupling a portion of the male reproductive structure adjacent the glans penis.

3. The method of claim 1, wherein elastically coupling the portion of the male reproductive organ to the support structure leaves at least seventy-five percent of the male reproductive organ exposed.

4. A method for compensating for male erectile dysfunction, comprising:
   positioning a penis over a splint having first and second ends, wherein the splint comprises a base adjacent a first end and an introducer adjacent a second end and an expandable coupler movably coupled to the splint so that the expandable coupler can be moved between the first and second ends to allow adjustment by the user, the expandable coupler having first and second openings, the first opening larger than the second opening, wherein the penis can be inserted through the first opening and the splint can be inserted through the second opening; and expandably mating a portion of the penis to the splint, wherein the penis can change erectile states.

5. The method of claim 4, wherein expandably mating a portion of the penis to the splint includes mating the portion of the penis to the expandable coupler.

6. The method of claim 5, wherein mating the portion of the penis to the expandable coupler includes inserting the penis through the first opening.

7. The method of claim 5, wherein inserting the penis through the first opening includes positioning the expandable coupler adjacent a glans penis portion of the penis.

8. The method of claim 5, wherein positioning the penis over the splint further includes inserting the penis through the base before inserting the penis through the first opening.

9. The method of claim 6, wherein positioning the penis over the splint further includes positioning a glans penis adjacent the introducer.

10. The method of claim 4, wherein premature ejaculation causes a change in the erectile state of the penis.

11. A method for manufacturing a male sexual aid, comprising:
providing a support structure having first and second ends;
forming a base adjacent the first end and an introducer adjacent the second end; and
coupling an elastic material adjacent the second end, wherein the elastic material is capable of covering less than half of a penis, the elastic material has first and second openings, the first opening larger than the second opening, and wherein coupling the elastic material includes inserting the support structure through the second opening to movably couple the elastic material to the support structure so that the elastic material can be moved between the first and second ends to allow adjustment by the user.

12. The method of claim 11, wherein forming the base includes forming an opening in the base wherein the opening is circular.

13. The method of claim 11, wherein coupling the elastic material includes providing the elastic material with an opening.

14. The method of claim 11, further including forming the base and the introducer as a unitary structure with the support structure.

15. An external penile splint, comprising:
a support having first and second ends;
a base adjacent the first end;
an introducer adjacent the second end; and
an elastic structure movably coupled to the support so that the elastic structure can be moved between the first and second ends to allow adjustment by the user, the elastic structure having first and second openings, the second opening smaller than the first opening, wherein the support passes through the second opening.

16. The external penile splint of claim 15, wherein the base and the first end form a unitary structure.

17. The external penile splint of claim 15, wherein the introducer and the second end form a unitary structure.

18. The external penile splint of claim 15, wherein the support comprises first and second support members having ends coupled to each other by the introducer.

19. The external penile splint of claim 18, further including a cross-member coupled between the first and second support members.

20. The external penile splint of claim 18, wherein the introducer comprises an inverted V-shaped structure having first and second ends, the first end coupled to the end of the first support member and the second end coupled to the end of the second support member, and wherein the inverted V-shaped structure has an apex that extends away from the first and second support members.

21. The external male splint of claim 15, wherein the introducer comprises a circular structure.

22. The external splint of claim 15, wherein the introducer comprises a basket structure.

23. The external splint of claim 15, wherein the support comprises a plastic.

24. The external splint of claim 15, further including a line wherein the line couples the elastic structure to the support.

25. An external penile splint comprising,
a support having first and second ends;
a base adjacent the first end;
an introducer adjacent the second end, wherein the introducer comprises:
a ring-shaped structure having first and second sides; and
a cross-member that extends from the first side of the ring-shaped structure to the second side of the ring-shaped structure, wherein the cross-member divides the ring-shaped structure into two portions; and
an elastic structure coupled adjacent the introducer.

26. The external penile splint of claim 25, wherein the elastic structure comprises:
a ring-shaped body; and
an elastic extension extending from one side of the ring-shaped body, the elastic extension having an end.

27. The external splint of claim 26, wherein the ring-shaped body is attached to the cross-member and the end of the elastic extension is attached to the second side of the ring-shaped structure of the introducer.

28. The external splint of claim 25, wherein the elastic structure is adhesively coupled adjacent the introducer.

29. The external male splint of claim 25, wherein the support comprises a plastic.

* * * * *

UNITED STATES PATENT AND TRADEMARK OFFICE
CERTIFICATE OF CORRECTION

| | | |
|---|---|---|
| PATENT NO. | : 7,611,456 B2 | Page 1 of 1 |
| APPLICATION NO. | : 11/535846 | |
| DATED | : November 3, 2009 | |
| INVENTOR(S) | : Roy A. Jared | |

It is certified that error appears in the above-identified patent and that said Letters Patent is hereby corrected as shown below:

Column 8:

Claim 2, line 53, replace "Organ" with --organ--.

Column 9:

Claim 7, line 14, replace "5" with --6--.
Claim 8, line 17, replace "5" with --6--.

Signed and Sealed this

Second Day of February, 2010

David J. Kappos
*Director of the United States Patent and Trademark Office*